United States Patent [19]
O'Donnell, Jr.

[11] Patent Number: 5,464,424
[45] Date of Patent: Nov. 7, 1995

[54] LASER ADJUSTABLE SUTURE

[76] Inventor: Francis E. O'Donnell, Jr., 709 The Hamptons, Town & Country, Mo. 63017

[21] Appl. No.: 265,747

[22] Filed: Jun. 27, 1994

[51] Int. Cl.$^6$ .................................................. A61B 17/04
[52] U.S. Cl. ........................ 606/228; 606/215; 606/232
[58] Field of Search .................................. 606/228–232; 428/34.9, 913; 524/88

[56] References Cited

U.S. PATENT DOCUMENTS

| | | |
|---|---|---|
| 3,126,680 | 3/1964 | Baird et al. . |
| 3,359,193 | 12/1967 | Pinner et al. . |
| 3,372,100 | 3/1968 | Charlesby et al. ........................ 428/36 |
| 4,596,728 | 6/1986 | Yang et al. ................................ 428/36 |

OTHER PUBLICATIONS

"Biaxial Orientation", Encyclopedia of Polymer Science & Technology, Interscience Publishers, John Wiley & Sons, vol. II, 1969.

*Primary Examiner*—Gary Jackson
*Attorney, Agent, or Firm*—Paul M. Denk

[57] ABSTRACT

A surgical suture having an elastic component that contracts under the application of laser energy to affect tightening of the suture. In one preferred embodiment the elastic component is a dome portion of a rivet. A first rivet has a concave dome portion and is attached to one end of a suture and a second rivet has a convex dome portion and is attached to the opposite end of the suture. Application of appropriate laser energy to either the concave or convex dome cause the dome to flatten thereby either loosening or tightening the suture. In another embodiment, the suture is formed of concentric fibers having a relatively non-elastic outer clad and a relatively elastic inner core. Application of laser energy to the clad causes the suture to elongate and loosen. Application of appropriate laser energy to the elastic core causes the inner core to contract and tighten the suture. In another embodiment, the suture has alternating segments of elastic and non-elastic material. Application of laser energy to the elastic material segment contracts the suture and application of laser energy to the non-elastic segments elongates and loosens the suture.

4 Claims, 1 Drawing Sheet

5,464,424

LASER ADJUSTABLE SUTURE

BACKGROUND OF THE INVENTION

This invention relates generally to surgical sutures, more specifically to a surgical suture that reacts appropriately to laser energy so that the tension on the suture can be adjusted by the application of laser energy, as well as to a method of adjusting the same.

Surgical sutures are well known to the art. Generally, nylon or cat-gut sutures are used to close a surgical wound. For the most part, surgical sutures can be loosened or tightened by untying the knot, drawing the suture tighter, and then retying the knot. In some situations, the suture must be snipped and retied or the suture must be removed and replaced. In delicate surgeries, for example ophthalmological surgery, it is quite difficult to adjust the tension on a suture once it is in place. The sutures placed in the eye are particularly fine. Adjusting the tension on the suture by conventional methods is painstaking and time consuming and can result in discomfort and inconvenience for the patient.

SUMMARY OF THE INVENTION

It is, therefore, a principle object of the present invention to provide a surgical suture that reacts to laser energy by becoming longer or shorter so that the tension on the suture can be adjusted by applying laser energy.

Another object of the present invention is to provide a surgical suture having a laser reactive rivet at each end of the suture so that laser energy applied to a convex portion of the rivet causes loosening of the suture and laser energy applied to a concave portion of the rivet tightens the suture.

Still another object of the present invention is to provide a concentric laser reactive suture having an inner core of elastic fiber that contracts under laser energy thereby tightening the suture and an outer portion that elongates under laser energy.

Still another object of the present invention is to provide a laser reactive suture having links of elastic material alternating with lengths of non-elastic material wherein laser energy applied to the elastic link causes a contraction of the suture and application of laser energy to the non-elastic material causes a lengthening of the suture.

In accordance with the invention, generally stated, a surgical suture is provided having an elastic component that contracts under the application of laser energy to effect tightening of the suture. In one preferred embodiment, the elastic component is a portion of a rivet. A first rivet, having a concave dome portion, is attached to one end of the suture and a second rivet, having a convex dome portion, is attached to the opposite end of the suture. Application of appropriate laser energy to the concave dome causes it to contract and flatten thereby drawing the suture tighter. Application of laser energy to the convex dome also causes it to contract and flatten, lessening tension on the suture. In another embodiment, the suture is formed of concentric fibers with an outer clad of a non-elastic material and an inner core of laser reactive elastic material. Application of laser energy to the clad causes the suture to elongate and loosen. Application of appropriate laser energy to the elastic core causes the elastic inner core to contract and draw the suture tighter. In another embodiment, the suture has alternating segments of elastic and non-elastic material. The elastic material contracts under the application of laser energy. The non-elastic material elongates under the application of laser energy. Selective application of laser energy to the appropriate segment will loosen or tighten the suture.

SUMMARY OF THE INVENTION

DESCRIPTION OF THE PREFERRED EMBODIMENT

Figure 1:
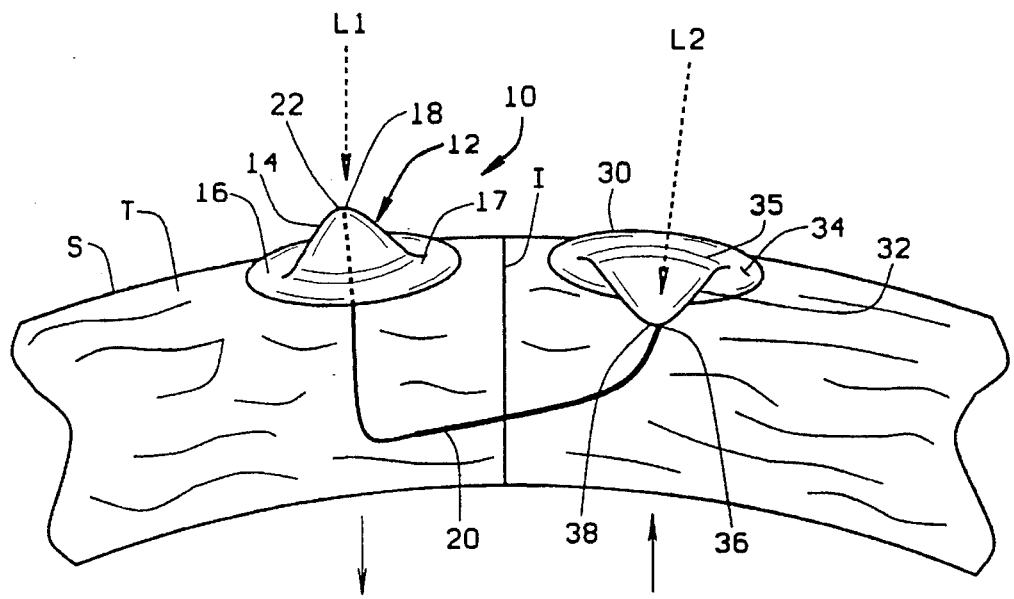
FIG. 1 is an enlarged cross section segment of eye tissue showing the application of an embodiment of the laser adjustable suture in its environment.

A laser adjustable suture constructed in accordance with the principles of the present invention is indicated generally by reference numeral 10 in FIG. 1. Suture 10 is shown applied through tissue T to close an incision I. Suture 10 has a first rivet 12 having a deformable conical portion or dome 14 which is convex relative to surface S of tissue T. Dome 12 is constructed from nylon, mersaline, prolene, polymethyl methacrylate or other appropriate elastic material that contracts in response to heat from a laser source. Rivet 12 has a radial flange 16 which extends outwardly from the base 17 of dome 14. Flange 16 allows for the appropriate attachment of the rivet to the tissue. An end 18 of an elongated suture 20 is appropriately attached to the inner apex 22 of dome 14.

A second rivet 30 is appropriately connected to an opposite end of suture 20. Rivet 30 has a deformable conical portion or dome 32. Dome 32 is concave relative to surface S of tissue T. Dome 32 is constructed from the appropriate laser reactive material previously described. Rivet 30 has a radial flange 34 at base 35 to allow the appropriate attachment of the rivet to the tissue T. End 36 of suture 20 is appropriately attached to the outer apex 38 of cone 32. To loosen the tension on suture 20, appropriate laser energy L1 is directed to cone 14. For example, an Argon laser at 200 mW for 0.2 seconds or less pulse duration can be used. Laser energy applied must be below the vaporization threshold of the dome material. Application of the appropriate energy of dome 14 causes dome 14 to contract or flatten moving downward towards surface S of tissue T. The attached suture 21 also moves downward in tissue T lessening the overall tension on suture 20. To tighten suture 20, appropriate laser energy L2 is focused on dome 32, causing dome 32 to contract or flatten drawing suture 20 upward toward surface S thereby increasing the overall tension on suture 20.

Figure 2:
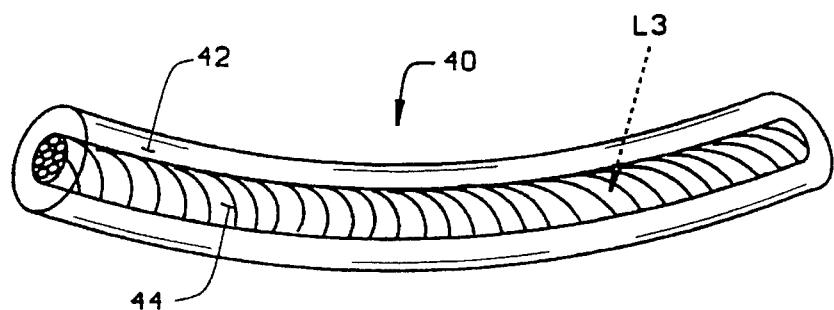
FIG. 2 is an enlarged segment of an alternative embodiment of a laser adjustable suture.

FIG. 2 illustrates an alternative embodiment of a laser adjusted suture of the present invention, indicated generally by reference numeral 40. Suture 40 is constructed from concentric fiber material. Suture 20 has an outer cladding 40 and a concentric inner fiber core 44. Outer cladding 42 is made of a transparent, relatively non-elastic material such as polyester. Inner fiber core 44 is constructed from relatively elastic, laser reactive deformable material such as nylon, mersaline, prolene or polymethyl methacrylate. It will be appreciated that core 44 is more elastic than cladding 42. Core 44 is darkly pigmented, for example, blue, black or purple so as to readily absorb laser energy. To tighten suture 40, laser energy L3 is focused on core 44. Core 44 is heated to a temperature below vaporization, causing core 44 to contract and tighten the suture. To effect more tightening, a sequence of laser spots is placed along the length of core 44.

To loosen suture 40, laser energy L3 is increased until core 44 breaks, relaxing some tension on suture 40. To effect more loosening, a plurality of breaks may be made along the length of core 44. Furthermore, laser energy may be directed to cladding 42 causing it to soften and elongate after core 44 is severed.

Figure 3:
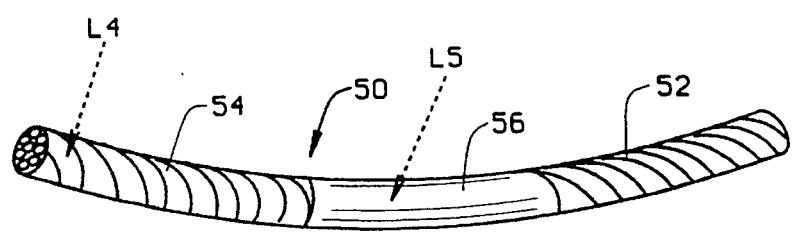
FIG. 3 is an enlarged segment of another alternative embodiment of the laser adjustable suture.

FIG. 3 illustrates another embodiment of the laser adjustable suture of the present invention, indicated generally by reference numeral 50. Suture 50 is comprised of alternating links or segments. Segments 52 and 54, for example, are comprised of a laser reactive, relatively elastic deformable material such as nylon, mersaline, prolene or polymethyl methacrylate. Segment 56 is comprised of a less elastic material, such as polyester. It will be appreciated that suture 50 can be constructed as long as needed and comprised of a plurality of alternating segments of material such as 54 and 56. In use, laser energy L4 is applied to elastic segments, such as 54. Laser energy L4 should be below the threshold for vaporization, for example, Argon laser at 200 mW for 0.2 seconds or shorter pulse duration. Application of laser energy L4 causes a contraction of the elastic material, thus tightening suture 50. To effect increased tightening of the suture, laser energy L4 can be applied to more than one elastic segment. Application of laser energy L5 to a non-elastic segment, such as 56, causes a weakening and lengthening of segment 56 and thus a lengthening of suture 50. This lengthening of the non-elastic segments results in less tension and loosening of the suture 50.

It will be appreciated by those skilled in the art that various changes and modifications may be made in the invention as described without departing from the scope of the appended claims. For example, various elastic or non-elastic materials may be substituted for those described. Moreover, other appropriate laser energy sources may be used as long as the energy applied elicits the appropriate response in the suture material. Furthermore, the relative dimensions of the respective elements of the sutures may vary depending upon the application of the suture. Therefore, the aforestated description and accompanying drawings should be viewed as illustrative only and not in a limiting sense.

I claim:

1. A laser adjustable suture comprising:

a length of suture material having a first end and a second end;

a rivet at said first end, said rivet having a deformable dome portion, said dome portion being convex, said first end of said suture being appropriately attached to said convex dome;

a second rivet, said second rivet having a deformable dome portion, said dome portion being concave, said second end of said suture being appropriately attached to said dome, said respective domes being reactive to laser energy so that said domes contract and flatten under the application of an appropriate laser energy source.

2. The laser adjustable suture of claim 1 wherein said respective domes are constructed from a relatively elastic material selected from a group consisting of nylon, prolene, mersaline, or polymethyl methacrylate.

3. The laser adjustable suture of claim 1 wherein said appropriate laser energy further comprises Argon laser at 200 mW for 2 seconds or shorter pulse duration.

4. A surgical suture assembly for use in ophthalmological surgery comprising:

a first rivet having a deformable portion, said deformable portion constructed of a material that reacts to laser energy;

a suture having a first end and a second end, said first end being connected to said first rivet;

a second rivet having a deformable portion, said deformable portion constructed from a material reactive to laser energy, said second rivet being attached to said second end of said suture so that laser energy directed to either said first or said second rivet causes said deformable portions to deform and change the tension on said interconnected suture.

* * * * *